US006238664B1

(12) United States Patent
Hellerbrand et al.

(10) Patent No.: US 6,238,664 B1
(45) Date of Patent: May 29, 2001

(54) PROCESS FOR STABILIZING PROTEINS

(75) Inventors: Klaus Hellerbrand, Geltendorf; Appollon Papadimitriou, Bichl; Gerhard Winter, Dossenheim, all of (DE)

(73) Assignee: Boehringer Mannheim GmbH, Mannheim (DE)

( * ) Notice: Subject to any disclaimer, the term of this patent is extended or adjusted under 35 U.S.C. 154(b) by 0 days.

(21) Appl. No.: 09/196,090

(22) Filed: Nov. 19, 1998

(30) Foreign Application Priority Data

Nov. 22, 1997 (EP) .................................................. 97120528
Feb. 19, 1998 (EP) .................................................. 98102846

(51) Int. Cl.[7] .............................. C12Q 1/34; C12N 9/96; C12N 5/02; G01N 33/53; A61K 39/395
(52) U.S. Cl. ...................... 424/130.1; 435/188; 435/963; 435/390; 530/387.1; 530/350; 530/380; 424/177.1
(58) Field of Search ..................................... 530/350, 380, 530/387.1, 390.5; 435/390.5, 188, 963, 18; 424/177.1, 130.1

(56) References Cited

U.S. PATENT DOCUMENTS 4,783,441   11/1988   Thurow .
5,429,928 *  7/1995   Blaustein et al. .

FOREIGN PATENT DOCUMENTS 0 018 609   11/1980   (EP) .
0 025 275    3/1981   (EP) .
0 314 095    5/1989   (EP) .
0 315 968    5/1989   (EP) .
0 318 081    5/1989   (EP) .
0670328A1 *  9/1995   (EP) .
0671410A1 *  9/1995   (EP) .

OTHER PUBLICATIONS

Derwent Abstract AN 98–555428 Abstract only Yu, R.M. et al RU 2109290 Apr. 20, 1998.
Chemical Abstracts No. 195334 Abstract only Heller MC et al 1997 Biotechnology Prog 13:590–596.
Heller, Biotechnol. Prog. 13 pp. 590–596 (1997).
Hwang, et al, Effect of Phosphate salts on the emulsion stability of soy protein isolate, J. Kor. Agric. Chem. Soc., vol. 35, No. 3, pp. 152–156 (1992).

* cited by examiner

Primary Examiner—David Saunders
Assistant Examiner—Amy DeCloux
(74) Attorney, Agent, or Firm—George W. Johnston; William H. Epstein

(57) ABSTRACT

An aqueous protein solution buffered with a potassium phosphate buffer, in which the ratio of potassium ions to sodium ions in the solution is at least 10:1, is resistant to the formation of protein aggregates and particles under conditions of freezing, thawing, lyophilization, and reconstitution.

45 Claims, 4 Drawing Sheets

PROCESS FOR STABILIZING PROTEINS

FIELD OF THE INVENTION

This invention is in the field of proteins and protein solutions.

BACKGROUND OF THE INVENTION

Proteins such as enzymes or antibodies as well as fragments thereof are unstable and susceptible to loss of activity and/or to formation of soluble or insoluble aggregates in aqueous solutions and when stored at low temperatures (below 0° C.) and in particular in repeated freezing and thawing processes and these aggregates become apparent by forming particles and thus as turbidities. However, such aggregate and/or particle formation cannot be tolerated or at least only in traces for pharmaceutical compositions of proteins. A pharmaceutical composition should be a clear solution and if it is present as a lyophilisate it should also lead to a clear particle-free solution when reconstituted which is also free of soluble protein aggregates.

Numerous processes and additives are known for the stabilization of proteins in solutions. For example the stabilization of proteins by adding heat-shock proteins such as HSP25 is for example described in EP-A 0 599 344. The stabilization of antibodies by adding block polymers composed of polyoxy-propylene and polyoxy-ethylene and by phospholipids is described in EP-A 0 318 081. EP-A 0 025 275 describes the stabilization of immunoglobulin by adding a salt of a basic substance containing nitrogen such as arginine, guanidine or imidazole. Other suitable additives for stabilization are polyethers (EP-A 0 018 609), glycerin, albumin and dextran sulfate (U.S. Pat. No. 4,808,705), detergents such as Tween®20 (DE 26 52 636, GB 8514349), chaperones such as GroEL (Mendoza, J. A. Biotechnol. Tech. 10 (1991) 535–540), citrate buffer (WO 93/22335) or chelating agents (WO 91/15509). Although these additives enable proteins to be stabilized to a certain extent in aqueous solutions. It has, however, turned out that none of the processes known in the prior art is suitable for stabilizing proteins during repeated freezing and thawing processes in such a way that no soluble or insoluble aggregates or only negligible amounts for therapeutic purposes are formed during rethawing, during storage at temperatures below 0° C. or when a solution is reconstituted after lyophilization.

In EP-A 0 314 095 a lyophilisate of a plasma protein such as factor VIII is described which contains histidine buffer as a buffer substance and calcium chloride as an additive and is present in a high ionic strength (0.35 to 1.2 mol/l NaCl).

A lyophilisate of a plasma protein such as factor VIII is described in EP-A 0 315 968 which contains 0.5 to 15 mmol/l sodium chloride or potassium chloride, 0.01 to 10 mmol/l lysine hydrochloride and 0.2 to 5 mmol/l histidine as a buffer ion. However, histidine buffer is not suitable for stabilizing proteins and for preventing aggregate and particle formation when lyophilisates of proteins are reconstituted.

SUMMARY OF THE INVENTION

This invention provides a composition comprising an aqueous buffered solution having a protein dissolved therein, wherein the solution contains potassium ions and either contains no sodium ions or contains sodium ions such that the ratio of potassium ions to sodium ions in the solution is at least 10:1; the solution being buffered with a potassium phosphate buffer.

This invention further provides a process for forming an aqueous buffered solution having a protein dissolved therein comprising: dissolving the protein in an aqueous solution; and adjusting the aqueous solution with a potassium phosphate buffer so that the aqueous solution having the protein dissolved therein contains potassium ions and either contains no sodium ions or contains sodium ions such that the ratio of potassium ions to sodium ions in the solution is at least 10:1.

The aqueous buffered protein solution of this invention is resistant to the formation of protein aggregation and particle formation under conditions of freezing, thawing, lyophilization, and reconstitution. Reduction of protein aggregation and particle formation is desirable during the manipulation of protein solutions generally, to reduce loss of protein and protein activity. It is also desirable in pharmaceutical uses, in which limiting the number of aggregates is particularly important.

DETAILED DESCRIPTION OF THE INVENTION

Figure 1:
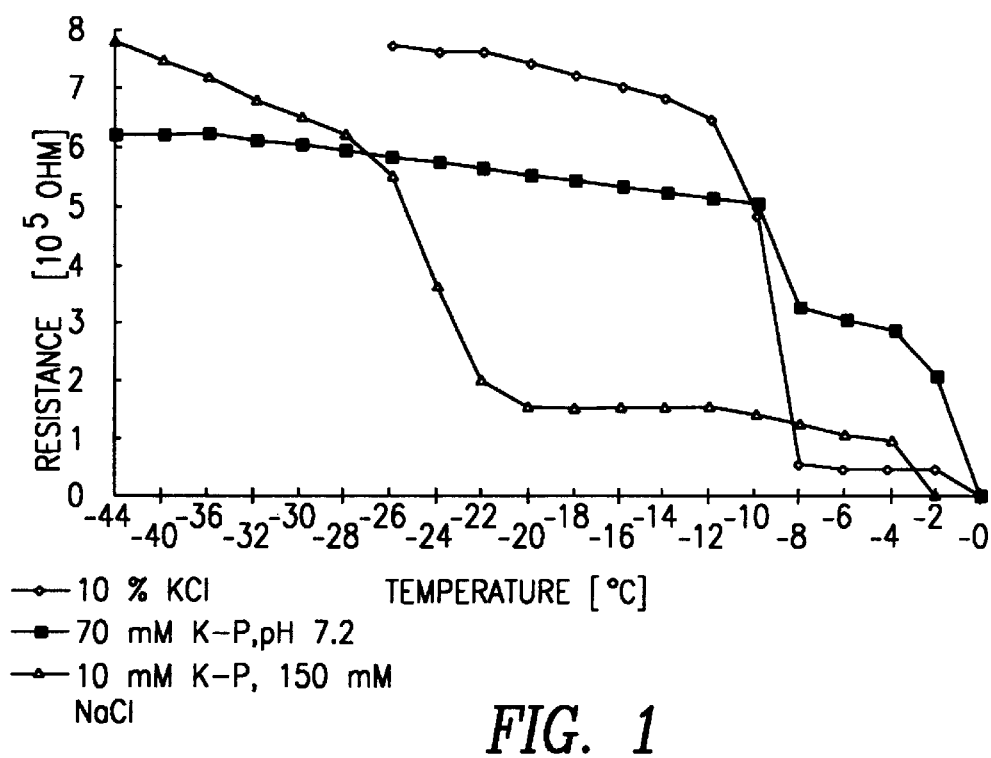
FIG. 1 shows the determination of the eutectic points of various buffers and salt solutions.

This invention provides a composition comprising an aqueous buffered solution having a protein dissolved therein, wherein the solution contains potassium ions and either contains no sodium ions or contains sodium ions such that the ratio of potassium ions to sodium ions in the solution is at least 10:1. In an embodiment of this invention the solution is buffered with a potassium phosphate buffer in a concentration of from 10 to 300 mmol/liter in the solution. In a more specific embodiment, the concentration of the potassium phosphate buffer in the solution is from 50 to 250 mmol/liter. In an embodiment the solution is at a pH of from 6 to 8 when measured at a temperature of from 4° C. to 30° C. In a more specific embodiment the pH of the solution is from 6.5 to 7.5 when measured at a temperature of from 4° C. to 30° C. In an embodiment of this invention the ratio of potassium ions to sodium ions is at least 50:1. Preferably the buffer is substantially free of sodium ions.

This invention also provides a process for forming an aqueous buffered solution having a protein dissolved therein comprising: a) dissolving the protein in an aqueous solution; and b) adjusting the aqueous solution with a potassium phosphate buffer so that the aqueous solution having the protein dissolved therein contains potassium ions and either contains no sodium ions or contains sodium ions such that the ratio of potassium ions to sodium ions in the solution is at least 10:1. After the buffered solution is formed, it can be frozen or lyophilized if desired, in accordance with conventional techniques. In a further embodiments, the frozen solution is thawed and the lyophilized solution is reconstituted.

In an embodiment of the composition and process of this invention the solution is buffered with a potassium phosphate buffer in a concentration of from 10 to 300 mmol/liter in the solution. In a more specific embodiment, the concentration of the potassium phosphate buffer in the solution is from 50 to 250 mmol/liter. In an embodiment the solution is at a pH of from 6 to 8 when measured at a temperature of from 4° C. to 30° C. In a more specific embodiment the pH of the solution is from 6.5 to 7.5 when measured at a temperature of from 4° C. to 30° C. In an embodiment of this invention the ratio of potassium ions to sodium ions is at least 50:1. Preferably the buffer is substantially free of sodium ions.

In accordance with this invention, any protein can be utilized. The specific identity of the protein is not critical, provided that an aqueous solution of the protein can be formed. In an embodiment of this invention the protein is an antibody. Furthermore, the concentration of the protein in the solution is not critical. Any amount of protein which can be dissolved in the aqueous buffered solution can be utilized. Typically, the concentration of protein which is dissolved in solution will be from 1 mg/ml to 50 mg/ml.

This invention provides a process for preventing the formation of protein aggregates in a solution of a pharmaceutical composition of a protein, preferably of an antibody, that is reconstituted from a lyophilisate wherein an aqueous buffered solution of the protein is frozen, thawed, divided into compartments of injectable amounts and these compartments are lyophilized which is characterized in that the aqueous buffered solution of the protein contains potassium phosphate buffer as a buffer substance and the ratio of potassium to sodium ions in the solution is 10:1 or larger. The aqueous buffer solution preferably contains essentially no sodium ions.

The invention enables pharmaceutical compositions of proteins, in particular proteins which have a tendency to dimerize or multimerize such as antibodies, to be formulated into. a stable pharmaceutical composition in a neutral pH range (pH 6–8, preferably pH 6.5–7.5). Proteins such as antibodies tend to aggregate in the neutral pH range especially if the solutions are frozen (optionally lyophilized) once or several times and thawed again.

A pharmaceutical composition is especially advantageous in potassium phosphate buffer in the pH range between 6 and 8, at a buffer concentration between 10 and 300 mmol/l, preferably between 50 and 250 mmol/l in which the lowest possible number of sodium ions are present in the pharmaceutical composition. A suitable ratio of potassium to sodium ions in the solution is 10:1 or more. It is particularly preferable that potassium phosphate buffer is used alone as the buffer substance in the pharmaceutical composition and no sodium salt (such as e.g. sodium chloride) is added. In such a case almost no sodium ions are present in the pharmaceutical composition or it only contains them in such low amounts that they do not cause formation of aggregates of proteins during repeated freezing or thawing.

It has turned out that lyophilisates of protein solutions which have been frozen at least once during the production process can then be reconstituted substantially without formation of turbidities if potassium phosphate buffer is used as the buffer substance. The usual buffers such as sodium phosphate buffer, histidine buffer or citrate buffer lead to the formation of aggregates in such a process which are mainly composed of the protein and thus also lead to turbidities to a considerable degree. The frozen protein solutions are already completely frozen through below ca. −15° C., have eutectic points above ca. −15° C. and can thus already be stored at this temperature or at lower temperatures preferably e.g. at −20° C. Since a solution is only completely frozen through below the eutectic temperature, this means that a protein in a phosphate buffer containing sodium ions is subjected to a higher stress during the frozen storage (usually at −20° C.) and during the freezing/thawing process than in a buffer free of sodium ions or in a buffer in which the sodium ion concentration is very low. According to the invention this stress is avoided in the above-mentioned formulations resulting in a suppression of aggregate and particle formation. This formulation enables a stable storage of the protein solution at −20° C. which can save costs. Potassium phosphate buffers in contrast to sodium phosphate buffers have only a slight pH shift (preferably at most ±1 pH unit, particularly preferably at most ±0.5 pH units) during the freezing process.

It has turned out that the concentration of the phosphate buffer should be at least 10 mmol/l, preferably about 50 mmol/l or higher in order to effectively prevent particle formation. Since the osmolarity should not be too high (it should advantageously be in the physiological range, preferably ca. 300 mOsm after reconstitution (±20 mOsm, a range of 100 to 500 mOsm is also suitable)) in pharmaceutical compositions (i.e. preferably in the reconstituted solution), the concentration of the buffer substance or optionally the sum of buffer substance and salt should be not more than 250–300 mmol/l. The buffer concentration is preferably between 50 and 250 mmol/l in the compartment. However, higher concentrations of buffer substance and/or salt can be tolerated in the production of the solutions (bulkware) used to produce the compartments.

If a salt additive is desired in the pharmaceutical composition especially to adjust the ionic strength, it is advantageous according to the invention to also not use sodium salts or to select a concentration of the sodium ions which is substantially lower than the concentration of the potassium ions. It is therefore expedient to add a potassium salt such as potassium chloride instead of the otherwise usual sodium chloride. However, it has turned out that low amounts of sodium salts (e.g. ca. 10 mmol/l or less) do not interfere provided the ratio of potassium ions to sodium ions is 10:1 or higher. It is not possible to add calcium salts such as e.g. calcium chloride since calcium phosphate is precipitated by such an addition and hence, apart from the formation of undesired turbidity, the buffer effect of the potassium phosphate according to the invention is abolished.

Non-soluble aggregates whose formation should be prevented in the process according to the invention are essentially understood as protein aggregates whose size is usually at least 1 $\mu$m but can also be in the range above 10 $\mu$m. The particles can be determined by suitable particle counting methods using commercial particle counting instruments such as e.g. the particle counting instrument AccuSizer 700 from PSS (Particle Sizing Systems, USA). According to the invention an improvement of the process is achieved when the number of particles between 2 and 400 $\mu$m/ml is <3000 or the number of particles between 10 and 400 $\mu$m/ml is 2000 or less. According to the USP (US-Pharmacopoeia) a maximum of 6000 particles in the range above 10 μm and a maximum of 600 particles in the range above 25 μm are allowed per injected dose of a pharmaceutical preparation. This can be achieved according to the invention in a simple manner for therapeutic compositions of proteins.

In accordance with this invention any protein can be utilized. The invention is based on the use of the aqueous buffered solution in accordance with this invention, and is not limited as to the specific protein dissolved therein. Proteins (polypeptides) are understood within the sense of the invention as naturally occurring and recombinant proteins or protein fragments as well as chemically modified proteins and proteins containing amino acid substitutions and additions. Proteins which are desirably stabilized for pharmaceutical compositions are preferably antibodies, antibody fusion proteins such as immunotoxins, enzymes and protein hormones such as erythropoietin, somatostatin, insulin, cytokines, interferons or plasminogen activators.

Compartments within the sense of the invention are understood as aliquots of the protein solution which, optionally after further processing (addition of further pharmaceutically acceptable substances), are suitable as pharmaceutical compositions preferably for injection in the patients.

The pH range in which the pharmaceutical composition is stabilized by the potassium phosphate buffer is preferably a slightly acidic, neutral or slightly alkaline range (ca. pH 6–8, preferably about pH 7).

According to the invention it is preferable to add a nonionic detergent such as polysorbate (e.g. Tween® 80), preferably at a concentration of at most 0.1% by weight and at least 0.01% by weight.

In addition it is preferable to add cryoprotectors or glass formers such as a non-reducing sugar (preferably sucrose or trehalose), advantageously at a concentration of at least 10 mg/ml, preferably of ca. 30–100 mg/ml.

Consequently a further subject matter of the invention is a low aggregate, meltable solid storage form of a protein which is essentially amorphous and is composed of a frozen solution of the protein and potassium phosphate buffer as the main buffer substance in which the ratio of potassium ions to sodium ions in the solution is at least 10:1.

Independent of the concentration of potassium ions and the residual content of sodium ions, the ratio of potassium to sodium ions should be at least 10:1, preferably at least 50:1. It is particularly preferable to use essentially sodium-ion-free potassium buffer.

In a further preferred embodiment of the invention the pharmaceutical composition contains a protein which has-been produced by an in vitro cell culture (for example recombinant production or culture of a hybridoma cell line to produce monoclonal antibodies). In this case it is expedient to either add potassium salt and/or potassium phosphate buffer with the first addition of salt or/and buffer, or to rebuffer at a later time in the isolation and purification process. This enables the interim stable storage of the polypeptide preparation below 0° C. Rebuffering is understood as an exchange of ions for example by dialysis. In the purification and isolation process of the protein the buffer or salt concentration can indeed be higher than 50–100 mmol/l before compartmentation since these compositions are not used therapeutically. However, it is essential that an osmolarity that is suitable for an injectable composition is adjusted before the compartmentation.

The disclosure of European Patent Application No. 97120528.1 is incorporated herein by reference.

The invention will be better understood by reference to the following examples. These Examples are illustrative, and do not limit the invention which is defined in the claims which follow thereafter.

EXAMPLE 1

Eutectic temperatures of various buffer and salt solutions

From FIG. 1 it is clear that the eutectic temperature of NaCl containing buffers is ca. 10° C. lower than that of NaCl-free buffers or solutions which contain KCl instead of NaCl. Since a solution is only completely frozen through below the eutectic temperature, this means that a protein in an NaCl-containing phosphate buffer is subjected to a higher stress than in NaCl-free buffer during frozen storage (usually at −20° C.) and during the freeze/thaw process. According to the invention this stress is avoided in the above-mentioned formulations which suppresses the formation of aggregates and particles. This formulation enables a stable storage of the protein solution at −20° C. by which means cost savings can be achieved.

EXAMPLE 2

Shift of the pH value during freezing of phosphate buffers

Figure 2:
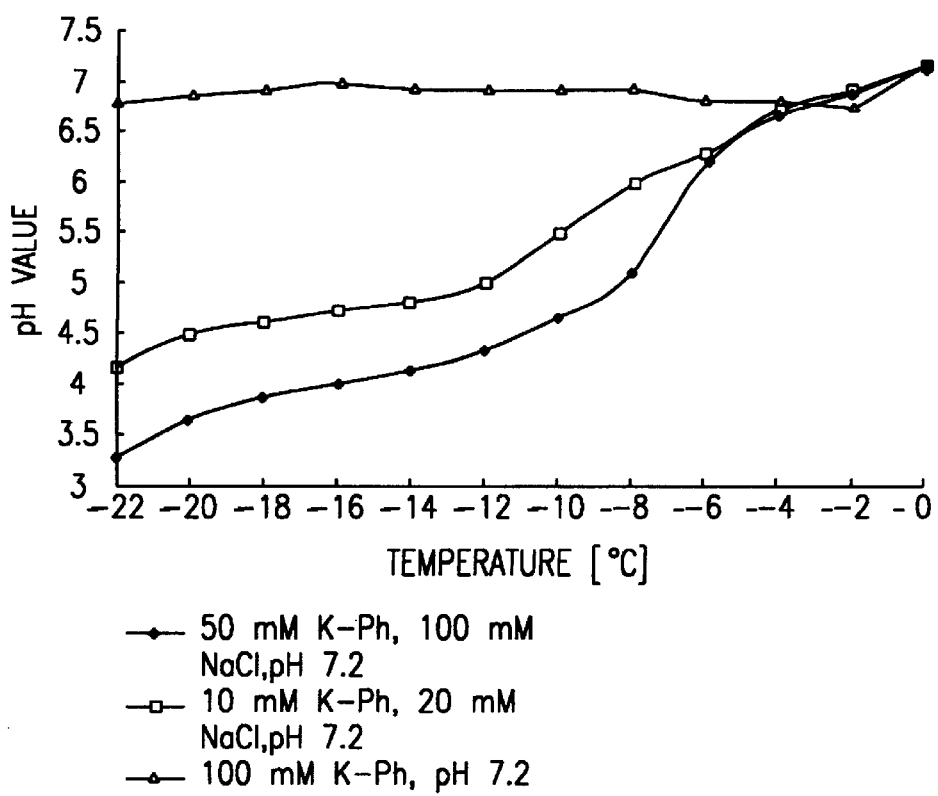
FIG. 2 shows the shift of the pH value during freezing of phosphate buffers.

It is clear from FIG. 2 that in NaCl-containing phosphate buffers the pH value greatly decreases during the freezing process due to precipitated disodium hydrogen phosphate. The pH value remains largely constant in NaCl-free potassium phosphate buffer.

EXAMPLE 3

Particle formation in protein solutions after shear or freeze/thaw stress

Solutions of a humanized IgG (antibody against L-selectin) in various buffers (A, B, C) were analysed for particle content (Accu Sizer, Particle Sizing Systems, USA):
A) AB in 10 mmol/l KP, 150 mmol/l NaCl, pH 7
B) AB in 100 mmol/l KP, pH 7.2
C) AB in 100 mmol/l KP, 0.01% by weight Tween®80, pH 7.2
  a) centrifuged (starting material)
  b) after shear stress (30 sec. vortexing)
  c) after six freeze/thaw cycles (−20° C.)
The data in FIG. 3 each refer to 0.7 ml sample.

Figure 3:
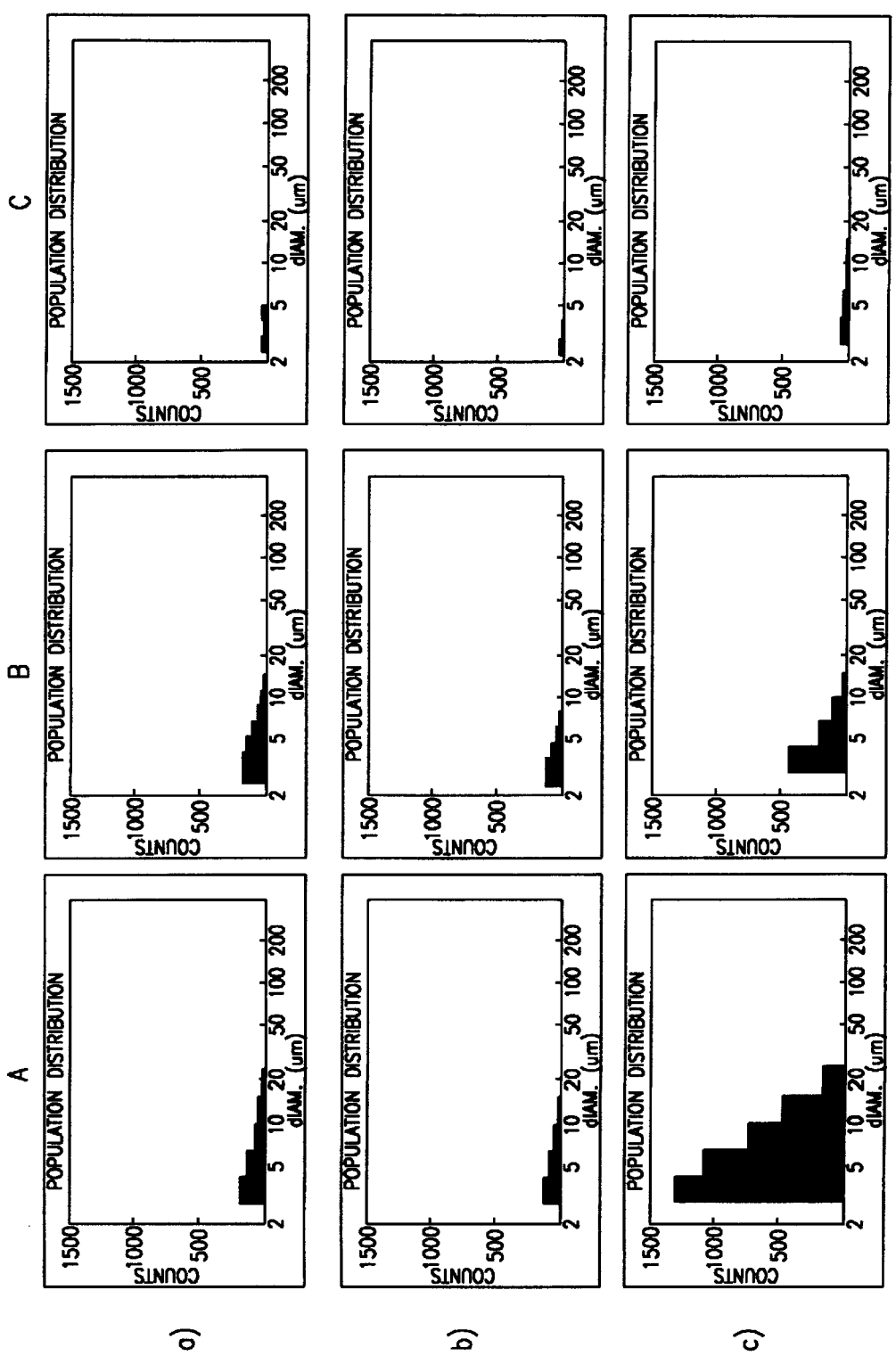
FIGS. 3A to 3C show the particle formation of solutions of an antibody (against L-selectin) in various buffer solutions (A, B, C) after shear or freeze/thaw stress. A: AB in 10 mmol/l KP, 150 mmol/l NaCl, pH 7; B: AB in 100 mmol/l KP, pH 7.2; C: AB in 100 mmol/l KP 0.01% by weight Tween®80, pH 7.2; a: centrifuged (starting material); b: after shearing stress (30 sec vortexing); c: after six freeze/thaw cycles (−20° C.).

It can be seen from FIG. 3 that particle formation is suppressed according to the invention by using sodium-free potassium phosphate buffers. This effect can be increased by the 5 addition of a nonionic detergent (Tween®80, 0.01% by weight).

EXAMPLE 4

Particle formation in protein solutions after shear or freeze/thaw stress

Solutions of an antibody against HBV in various buffers (A, B, C) were analysed for particle content (Accu Sizer, Particle Sizing Systems):
A) AB in 10 mmol/l KP, 30 mmol/l NaCl, pH 6.5
B) AB in 100 mmol/l KP, pH 7.2
C) AB in 100 mmol/l KP, 0.01% by weight Tween®80, pH 7.2
  a) centrifuged (starting material)
  b) after shear stress (30 sec. vortexing)

c) after six freeze/thaw cycles (−20° C.)

The data in FIG. 3 each refer to 0.7 ml sample.

Figure 4:
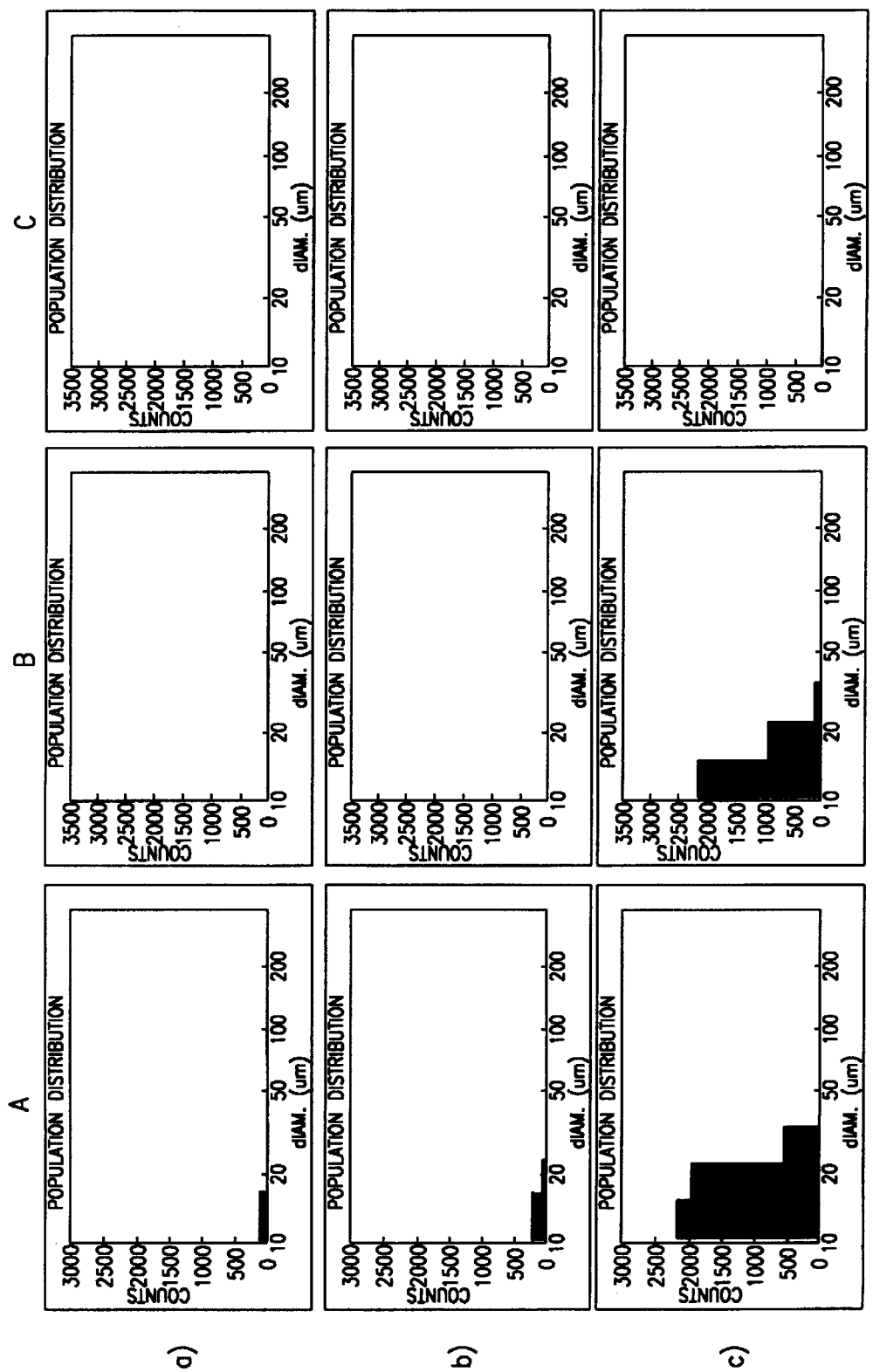
FIGS. 4A to 4C show the particle formation of solutions of an antibody against HBV in various buffer solutions (A, B, C) after shear or freeze/thaw stress. A: AB in 10 mmol/l KP, 30 mmol/l NaCl, pH 6.5; B: AB in 100 mmol/l KP, pH 7.2; C: AB in 100 mmol/l KP, 0.01% by weight Tween® 80, pH 7.2.

It can be seen from FIG. 4 that particle formation is suppressed according to the invention by using sodium-free potassium phosphate buffers. This effect can be increased by the addition of a nonionic detergent.

EXAMPLE 5

Prevention of the formation of soluble aggregates during the storage of protein solutions (humanized IgG according to example 3) at temperatures below 0° C.

Figure 5A:
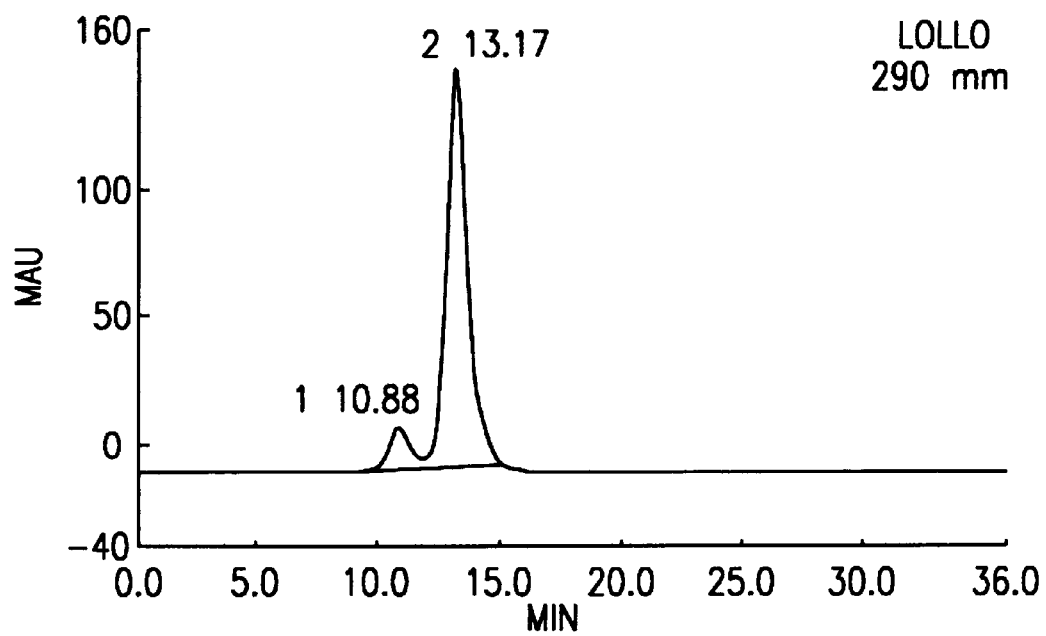
FIGS. 5A to 5B show the size exclusion HPLC analysis of soluble aggregates in protein solutions (humanized IgG according to example 3) after storage at temperatures below 0° C. A: AB in 10 mmol/l KP, 150 mmol/l NaCl, pH 7.0; B: AB in 100 mmol/l KP, pH 7.2.
Figure 5B:
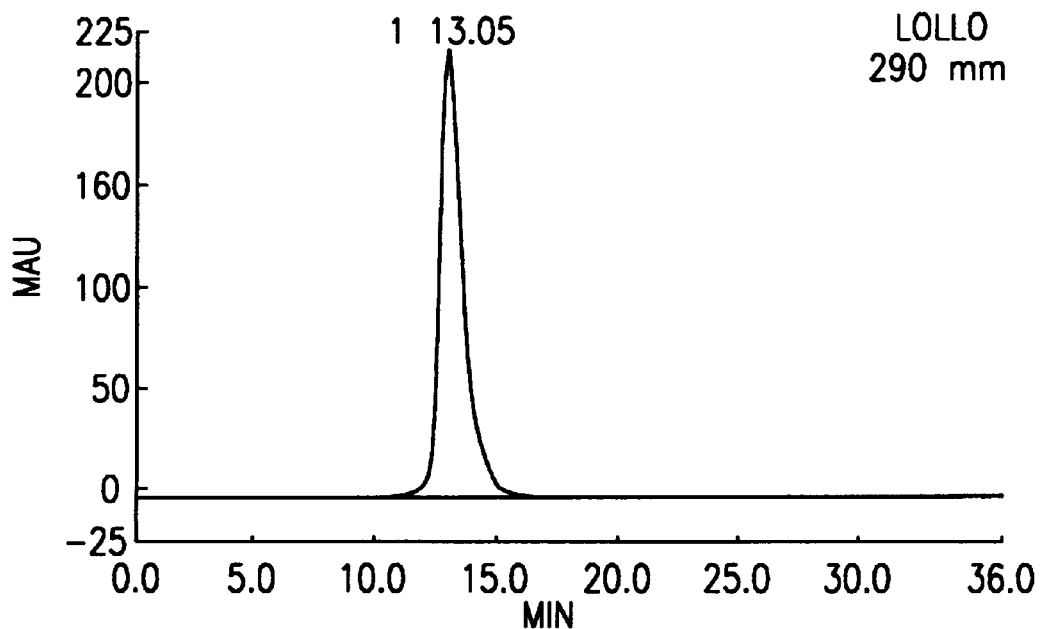

Protein solutions were stored for several weeks at −20° C. in A) 10 mM potassium phosphate, 150 mM NaCl, pH 7.0, and B) in 100 mM potassium phosphate, pH 7.2. Analysis of the soluble aggregates and the native protein was carried out by size exclusion HPLC (FIG. 5). According to the invention considerably fewer protein aggregates occur in the NaCl-free buffer than in the NaCl-containing buffer. This is above all due to the fact that a shift of the pH value is substantially prevented in the NaCl-free buffer and the storage temperature is considerably below the eutectic temperature. (see also examples 1 and 2).

EXAMPLE 6

Particle formation in protein solutions after freeze/thaw stress

The antibodies MAB L-selectin, MAB HBV; MAB PDGF-R and MAB LNGF-R in various buffers were analysed for particle content before and after freeze/thaw stress (6×freezing/thawing) (Accu Sizer, Particle Sizing Systems) (results cf. table 1, $C_{prot}$: protein concentration). Particles with a size of 2–400 μm per ml are stated. It is clear that the particle formation is suppressed according to the invention by using sodium-free potassium phosphate buffers (KP). This effect can be increased by adding a nonionic detergent.

TABLE 1

| | $C_{prot}$ [mg/ml] | particles/ml without stress 2-400 μm | Particles/ml 6 × freezing/ thawing 2-400 μm |
|---|---|---|---|
| MAB L-selectin in buffer | | | |
| 10 mM KP, 150 mM NaCl, pH 7.2 | 21.40 | 875 | 6245 |
| 100 mM KP, 0.01% by weight Tween80, pH 7.2 | 18.50 | 276 | 332 |
| MAB HBV in buffer | | | |
| 10 mM KP, 30 mM NaCl, pH 6.6 | 17.85 | 544 | 19085 |
| 100 mM KP, 0.01% by weight Tween80, pH 7.2 | 18.30 | 740 | 695 |
| MAB PDGF-R in buffer | | | |
| 10 mM KP, 150 mM NaCl, pH 7.2 | 1.70 | 130 | 33795 |
| 50 mM KP, 0.01% by weight Tween80, pH 7.2 | 1.70 | 691 | 677 |
| MAB LNGF-R in buffer | | | |
| 10 mM KP, 150 mM NaCl, pH 7.2 | 1.70 | 690 | 28915 |
| 50 mM KP, 0.01% by weight Tween80, pH 7.2 | 1.70 | 1164 | 1257 |

What is claimed is:

1. In a process for reconstituting a lyophilizate formed from an aqueous solution having a protein dissolved therein, the improvement comprising:
   wherein the solution contains potassium ions and either contains no sodium ions or contains sodium ions such that the ratio of potassium ions to sodium ions in the solution is at least 10:1; and
   the solution being buffered at a pH from 6 to 8 with a potassium phosphate buffer in a concentration of from 10 to 300 mmol/liter in the solution.

2. The process of claim 1 wherein the protein is an antibody.

3. The process of claim 1 wherein the dissolved protein is present in the solution in a concentration from 1 mg/ml to 50 mg/ml.

4. The process of claim 1 wherein the concentration of the potassium phosphate buffer in the solution is from 50 to 250 mmol/liter.

5. The process of claim 1 wherein the pH of the solution is from 6.5 to 7.5 when measured at a temperature of from 4° C. to 30° C.

6. The process of claim 1 wherein the osmolarity of the solution is from 100 to 500 mOsm.

7. The process of claim 6 wherein the osmolarity of the solution is from 280 mOsm to 320 mOsm.

8. The process of claim 1 wherein the ratio of potassium ions to sodium ions in the solution is at least 50:1.

9. The process of claim 1 wherein the buffer is substantially free of sodium ions.

10. In a process for thawing a frozen aqueous solution formed from a liquid aqueous solution having a protein dissolved therein, the improvement comprising:
    wherein the liquid aqueous solution contains potassium ions and either contains no sodium ions or contains sodium ions such that the ratio of potassium ions to sodium ions in the solution is at least 10:1; and
    the liquid aqueous solution being buffered at a pH from 6 to 8 with a potassium phosphate buffer in a concentration of from 10 to 300 mmol/liter in the liquid aqueous solution.

11. The process of claim 10 wherein the protein is an antibody.

12. The process of claim 10 wherein the dissolved protein is present in the liquid aqueous solution in a concentration from 1 mg/ml to 50 mg/ml.

13. The process of claim 10 wherein the concentration of the potassium phosphate buffer in the liquid aqueous solution is from 50 to 250 mmol/liter.

14. The process of claim 10 wherein the pH of the liquid aqueous solution is from 6.5 to 7.5 when measured at a temperature of from 4° C. to 30° C.

15. The process of claim 10 wherein the osmolarity of the liquid aqueous solution is from 100 to 500 mOsm.

16. The process of claim 15 wherein the osmolarity of the liquid aqueous solution is from 280 mOsm to 320 mOsm.

17. The process of claim 10 wherein the ratio of potassium ions to sodium ions in the liquid aqueous solution is at least 50:1.

18. The process of claim 10 wherein the buffer is substantially free of sodium ions.

19. A process for forming a frozen aqueous buffered solution having a protein dissolved therein comprising:

a) dissolving the protein in a liquid aqueous solution; and b) adjusting the liquid aqueous solution with a potassium phosphate buffer so that the liquid aqueous solution having the protein dissolved therein contains potassium ions and either contains no sodium ions or contains sodium ions such that the ratio of potassium ions to sodium ions in the liquid solution is at least 10:1;

is buffered with the potassium phosphate buffer in a concentration of from 10 to 300 mmol/liter; and is at a pH of from 6 to 8 when measured at a temperature of from 4° C. to 30° C.; and c) freezing the liquid aqueous buffered solution.

20. The process of claim 19 wherein the protein is an antibody.

21. The process of claim 19 wherein the dissolved protein is present in the liquid aqueous solution in a concentration from 1 mg/ml to 50 mg/ml.

22. The process of claim 19 wherein the concentration of the potassium phosphate buffer in the liquid aqueous solution is from 50 to 250 mmol/liter.

23. The process of claim 19 wherein the pH of the liquid aqueous solution is from 6.5 to 7.5 when measured at a temperature of from 4° C. to 30° C.

24. The process of claim 19 wherein the osmolarity of the liquid aqueous solution is from 100 to 500 mOsm.

25. The process of claim 24 wherein the osmolarity of the liquid aqueous solution is from 280 mOsm to 320 mOsm.

26. The process of claim 19 wherein the ratio of potassium ions to sodium ions in the liquid aqueous solution is at least 50:1.

27. The process of claim 19 whereein the buffer is substantially free of sodium ions.

28. A process for forming a lyophilizate of a protein, comprising:

a) dissolving the protein in an aqueous solution; and b) adjusting the aqueous solution with a potassium phosphate buffer so that the aqueous solution having the protein dissolved therein contains potassium ions and either contains no sodium ions or contains sodium ions such that the ratio of potassium ions to sodium ions in the solution is at least 10:1;

is buffered with potassium phosphate buffer in a concentration of from 10 to 300 mmol/liter; and is at a pH of from 6 to 8 when measured at a temperature of from 4° C. to 30° C.; and c) lyophilizing the aqueous buffered solution.

29. The process of claim 28 wherein the protein is an antibody.

30. The process of claim 28 wherein the dissolved protein is present in the aqeuous solution in a concentration from 1 mg/ml to 50 mg/ml.

31. The process of claim 28 wherein the concentration of the potassium phosphate buffer in the solution is from 50 to 250 mmol/liter.

32. The process of claim 28 wherein the pH of the solution is from 6.5 to 7.5 when measured at a temperature of from 4° C. to 30° C.

33. The process of claim 28 wherein the osmolarity of the solution is from 100 to 500 mOsm.

34. The process of claim 33 wherein the osmolarity of the solution is from 280 mOsm to 320 mOsm.

35. The process of claim 28 wherein the ratio of potassium ions to sodium ions is at least 50:1.

36. The process of claim 28 wherein the buffer is substantially free of sodium ions.

37. In a process for preventing the formation of protein aggregates in a reconstituted lyophilisate of a pharmaceutical composition of a protein, wherein an aqueous buffered solution of the protein is frozen, the frozen aqueous buffered solution is thawed, the thawed solution is divided into compartments of injectable amounts, the compartments of injectable amounts are lyophilized, and the lyophilized injectable amounts are reconstituted; the improvement comprising the aqueous buffered solution of the protein comprises potassium buffer as a buffer substance and the ratio of potassium to sodium ions in the solution is 10:1 or higher.

38. The process of claim 37, wherein the buffer concentration in the compartment is between 10 mmol/l and 300 mmol/l.

39. The process of claim 37, wherein the osmolarity of the reconstituted solution of the compartment is between 100 and 500 mOsm.

40. The process of claim 39 wherein the osmolarity of the reconstituted solution of the compartment is 300 ±50 mOsm.

41. The process of claim 37, wherein the aqueous buffered solution is buffered in the pH range between 6–8.

42. The process of claim 37, wherein the aqueous buffered solution further comprises a nonionic detergent.

43. The process of claim 37, wherein the aqueous buffered solution further comprises a sugar at a concentration of 10–100 mg/ml.

44. The process of claim 37, wherein the protein is an antibody.

45. The process of claim 37 wherein the protein is present in the aqueous buffered solution prior to freezing in a concentration from 1 mg/ml to 50 mg/ml.

* * * * *